United States Patent [19]

Dryden, Jr. et al.

[11] 4,057,542
[45] Nov. 8, 1977

[54] PROCESS FOR THE PREPARATION OF 17β-HYDROXY-3-OXO-17α-PREGN-4-ENE-21-CARBOXYLIC ACID γ-LACTONE

[75] Inventors: Hugh L. Dryden, Jr., Deerfield; Mike G. Scaros, Arlington Heights; Thomas J. Telinski, Chicago, all of Ill.

[73] Assignee: G. D. Searle & Co., Chicago, Ill.

[21] Appl. No.: 718,643

[22] Filed: Aug. 30, 1976

[51] Int. Cl.$^2$ ............................................. C07J 21/00
[52] U.S. Cl. ..................... 260/239.55 C; 260/239.57; 260/239.5
[58] Field of Search ................... 260/239.55 C, 239.57

[56] References Cited

U.S. PATENT DOCUMENTS

| | | | |
|---|---|---|---|
| 3,474,115 | 10/1969 | Buzby, Jr. et al. | 260/397.1 |
| 3,758,517 | 9/1973 | Edwards | 260/397.4 |

OTHER PUBLICATIONS

Rec. Trav. Chem. (7) vol. 88, (1969) pp. 752–765.

*Primary Examiner*—Elbert L. Roberts
*Attorney, Agent, or Firm*—John J. Kolano

[57] ABSTRACT

A new process for the preparation of 17β-hydroxy-3-oxo-17α-pregn-4-ene-21-carboxylic acid γ-lactone is described herein. The process makes use of androst-4-ene-3,17-dione as the starting material and 17α-ethynyl-17β-hydroxyandrost-4-en-3-one as an early intermediate.

11 Claims, No Drawings

PROCESS FOR THE PREPARATION OF 17β-HYDROXY-3-OXO-17α-PREGN-4-ENE-21-CARBOXYLIC ACID γ-LACTONE

The present invention relates to a new process for the preparation of 17β-hydroxy-3-oxo-17α-pregn-4-ene-21-carboxylic acid γ-lactone using b 17α-ethynyl-17β-hydroxyandrost-4-en-3-one as an intermediate. In a further aspect of the present invention, the 17α-ethynyl-17β-hydroxyandrost-4-en-3-one used as an intermediate is obtained from androst-4-ene-3,17-dione by a new process.

In the synthesis of chemical compounds and, particularly, in the synthesis of steroids, a vareity of procedures can often be used to prepare a particular compound. Thus, a particular reaction sequence may be developed and used for the preparation of a commercially desired valuable compound based on the availability of a particular steroid raw material. However, this same reaction sequence may not be applicable if it becomes necessary to rely on raw materials from other sources and it may be necessary to find an entirely new procedure in order to make use of other new materials and avoid reliance on a single source. Thus, a steroid starting material that has recently become available in large quantities from the fermentation of sitosterol is androst-4-ene-3,17-dione but the previously known procedures are not applicable for the conversion of this material to 17β-hydroxy-3-oxo-17α-pregn-4-ene-21-carboxylic acid γ-lactone. But a new procedure has been found, whereby androst-4-ene-3,17-dione is first converted to 17α-ethynyl-17β-hydroxyandrost-4-en-3-one and then 17α-ethynyl-17α-hydroxyandrost-4-en-3-one is further subjected to a series of reactions to give 17β-hydroxy-3-oxo-17α-pregn-4-ene-21-carboxylic acid γ-lactone. This compound is a particularly useful and valuable starting material for the preparation of spironolactone, a commercially marketed compound which is useful as a diuretic and an anti-hypertensive agent.

As indicated earlier, steroids are susceptible of preparation by a wide variety of reactions or reaction paths. However, in spite of the fact that a variety of reaction paths may be available, this does not necesarily mean that a practical series of reactions can be developed for the prepartion of large quantities of a particular desirable steroid product. Thus, for example, a particular reaction may give good yields and proceed smoothly so that it would be particularly attractive for use in one stage of a synthetic sequence but it may introduce functional groups or contaminants which would cause substantial problems at other stages in the reaction sequence so as to make the particular overall process impractical. So, it is necessary to take into consideration all stages of a multi-step synthetic sequence in order to obtain an overall procedure that is suitable.

Thus, the process of the present invention makes maximum use of steroid raw materials by keeping side reactions to a minimum, or by avoiding processes which involve significant side reaction, or by adapting the process so that any significant products of side reactions can still be subjected to subsequent reactions in the same manner as the main product so as to ultimately give the desired product too. The present process is further advantageous in that it allows for the ready removal of any minor by-products that may be formed or it allows for the ready removal of impurities that may be present in the initial starting material. The present process is still further advantageous in that it makes use of soluble intermediates or, where the particular intermediates may not be soluble, the particular reaction involved may still be carried out using a relatively concentrated suspension of materials so that a high throughput of material is maintained through the process. The reaction sequence further serves to minimize as much as possible the use of expensive reactants or solvents or to permit the possible recovery of solvents which are used on a large scale. With all of the advantages set forth above, the present invention provides a particularly useful and commercially feasible process for the preparation of 17β-hydroxy-3-oxo-17α-pregn-4-ene-21-carboxylic acid γ-lactone.

The specific details of the present process are as follows. The 3-carbonyl group of androst-4-ene-3,17-dione is selectively converted to the corresponding enamine, preferably the pyrrolidine enamine, and the resulting product is ethynylated using acetylene and potassium hydroxide to give the corresponding 17-ethynyl compound. The enamine group is removed to give 17α-ethynyl-17β-hydroxyandrost-4-en-3-one.

In the next phase of the process, the two oxygen functional groups in 17α-ethynyl-17β-hydroxyandrost-4-en-3-one are protected so that they will not be affected during the later reactions. Specifically, the 3-ketone is converted to the corresponding vic-(lower alkylene) ketal using an appropriate vic-glycol. The vic-(lower alkylene) group and the vic-glycol each contain up to 6 carbon atoms and any such ketal is satisfactory although the ethylene ketal is particularly preferred and the propylene ketal is also advantageous. During ketal formation, there is shifting of the double bond from the 4-position to the 5-position although a considerable amount (about 25%) of the product ketal still has the double bond in the 4-position. Thus, when reference is made to a 5-unsaturated compound or a (5- or 4-)ene, this means that the material is the 5-unsaturated compound but may contain up to about 25% of the corresponding 4-unsaturated compound.

The ketal is then reacted with a (lower alkyl) vinyl ether to give the corresponding 17-[1-(lower alkoxy)ethoxy] compound wherein the 5-unsaturated compound has the following formula

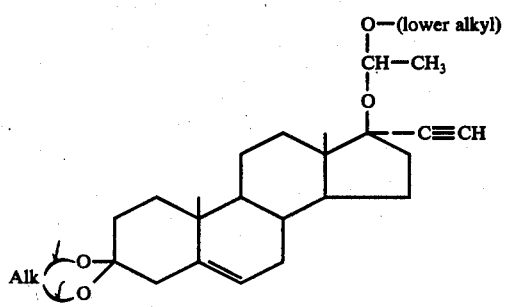

wherein Alk is a vic-(lower alkylene) group. The lower alkyl portion of the above steroid product and also the vinyl ether starting material contains up to 6 carbon atoms and can be exemplified by groups such as methyl, ethyl, propyl or butyl although the butyl compound is particularly preferred. The reaction is carried out under slightly acidic conditions which do not disturb the ketal function appreciably. Methanesulfonic acid is particularly useful for this purpose although other acids of similar strength can be used. The indicated product is then converted to the corresponding 21-lithium product or 21-magnesium halide product by standard procedures such as treatment with an alkyllithium or a Grignard reagent. Particularly preferred lithium compounds are lower alkyllithiums such as butyllithium. Particularly preferred Grignard reagents are methylmagnesium halides such as methylmagnesium chloride. The resulting steroidal organometallic compound is then converted to the corresponding propargylic acid salt by treatment with carbon dioxide. The acid salt is then converted to the corresponding methyl ester by treatment with dimethyl sulfate although, in the case of the magnesium chloride product, it is necessary to convert the original salt to the corresponding potassium salt before the indicated methyl ester is prepared. The resulting ester is then carefully treated with acid to remove the 17-protecting group. This hydrolysis is usually carried out in the presence of excess glycol corresponding to that which formed the 3-ketal. This provides for ready complexing of the reaction by-products from the hydrolysis and helps assure that the 3-ketal stays in its original form. The 5-unsaturated product involved here has the following formula

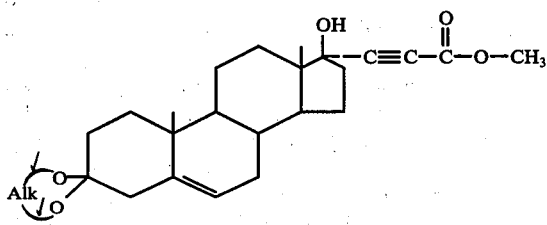

wherein Alk is defined as above. The indicated product is then hydrogenated using a nickel catalyst. Useful catalysts for this reduction are nickel boride or nickel on alumina. The reduction can be carried out under strongly alkaline conditions. In that case, the 21-carboxylic acid is hydrolyzed to the salt in addition to the triple bond being hydrogenated to give the corresponding saturated compound. Depending on the specific reaction conditions used in the alkaline process, the salt obtained can be an alkali metal salt such as the lithium salt or an ammonium salt such as the tetramethylammonium salt. Acidification of the resulting hydrogenation mixture gives the lactone and, at the same time, the 3-ketal is hydrolyzed back to the 3-ketone with the 5-double bond shifting back to the 4-position.

Use of the pyrrolidine enamine in the preparation of 17α-ethynyl-17β-hydroxyandrost-4-en-3-one has a number of advantages. Thus, this particular enamine forms quite readily as compared to the procedures needed to prepare other enamines. In addition, the pyrrolidine enamine precipitates readily and thus permits ready separation from impurities that may be present in the initial starting material. As a result, it is possible to use crude androst-4-ene-3,17-dione. A further advantage in this process is the fact that, even though the materials involved in the ethynylation step may be relatively insoluble, it is still possible to carry out the procedure using a fairly concentrated suspension so that this process permits a better throughput than may be possible with other alternative methods for bringing about this conversation.

For the conversion of 17α-ethynyl-17β-hydroxyandrost-4-en-3-one to 17β-hydroxy-3-oxo-17α-pregn-4-ene-21-carboxylic acid γ-lactone, the most feasible procedures involve the use of organometallic reagents but this then necessitates protecting the 3-ketone and the 17-hydroxy group which would be affected by such reagents and would thus complicate the reaction is not protected. Actually, it would not be absolutely necessary to protect the 17-hydroxy group but, in the absence of such protection, it would be necessary to use additional organometallic material to allow for the formation of the salt of the 17-hydroxy group. However, because of the relative insolubility of the salt, the throughput possible would be reduced considerably. In addition, deethynylation could occur. With a protecting group at the 17-position, the use of extra organometallic material is avoided and a more soluble compound is obtained so that further reactions can be carried out with much less difficulty.

As noted earlier, when the 3-ketal is formed, much of the resulting product contains the double bond shifted to the 5-position although a considerable amount of the 4-double bonded material is present. This causes some complications since, although a Δ⁵-compound is relatively stable and not particularly susceptible to other reactions, the Δ⁴-compound is quite sensitive to acid and the presence of small amounts of acid converts the ketal back to the 3-ketone and thus defeats the original intention of providing a protecting group for the 3-ketone. Such a complication could be avoided by separating out the Δ⁴-ketal at this point, but this presents a number of separate problems so that the present process has been specifically adapted so as to avoid the use of reactions or conditions which would hydrolyze the Δ⁴-ketal and in this way avoiding the need to separate out this material before carrying out processes on material in which it may be present.

As noted earlier, the hydrogenation can be carried out under alkaline conditions so that a number of reactions may be taking place essentially simultaneously. Thus, this particular step should not be limited to any particular order in which hydrogenation or hydrolysis may occur.

The following examples are presented to further illustrate the present invention. They should not be construed as limiting it in any way. In these examples, quantities are indicated in parts by weight unless parts by volume are specified, and temperatures are indicated in degrees Centigrade (°C.). The relationship between parts by weight and parts by volume is the same as that existing between grams and milliliters.

EXAMPLE 1

A solution of 113.5 parts of crude androst-4-ene-3,17-dione in 427 parts of methanol is heated to just below reflux temperature. To the resulting stirred solution there is added 4.3 parts of pyrrolidine. After five minutes, more pyrrolidine is added at a steady rate so that 33.2 parts are added over a period of 25 minutes. The warm mixture is then stirred for an additional 15 minutes before it is cooled to 5°–10° C. The solid product which formed during the reaction is then separated by filtration and washed several times with methanol at 10° C. The solid is then dried to give 3-(1-pyrrolidinyl)androsta-3,5-dien-17-one melting at about 217°–220° C.

EXAMPLE 2

A slurry is prepared from 351 parts of tetrahydrofuran, 85 parts of 90% potassium hydroxide powder and 0.6 part of ethylenediamine tetraacetic acid. The resulting slurry is stirred and 17.6 part of ethanol is added. The mixture is then warmed to 40° C. and stirred at the temperature for 30 minutes. The resulting slurry is then cooled to −10° C. and 95.6 parts of 3-(1-pyrrolidinyl)androsta-3,5-dien-17-one is added, maintaining the mixture under nitrogen. Then, 10.9 parts of acetylene is added to the mixture over a period of 3 hours. It is then stirred for one hour at a temperature of −10° C. or lower. Then, a mixture of 81.4 parts of glacial acetic acid and 122 parts of water is added while the temperature of the reaction mixture is maintained below 10° C. When the addition is nearly completed, the temperature is allowed to rise to 30° C. Stirring is stopped and the liquid layers are separated. The aqueous layer is extracted with tetrahydrofuran and the resulting organic extract is combined with the organic layer from the reaction mixture. To this resulting organic solution is added a solution of 26 parts of boric acid in 85 parts of water. The mixture is refluxed for one hour and the tetrahydrofuran is distilled off at atmospheric pressure while 350 parts of water is added. Once all of the tetrahydrofuran has been distilled off, an additional 197 parts of water is added. The mixture is then cooled to about 30°–35° C., the solid is separated by filtration and washed until the filtrate is neutral. The solid is then dried to give 17α-ethynyl-17β-hydroxyandrost-4-en-3-one melting at about 264.5°–269° C.

The crude material is mixed with 2.5 parts of boric acid, 2.3 parts of water and 205 parts of methanol and refluxed for 30 minutes. It is then cooled slightly, 1.39 parts of concentrated hydrochloric acid is added, and the mixture is stirred and refluxed for one hour. The mixture is then cooled to 20° C. and the precipitated solid is separated by filtration and washed with methanol and finally dried at 60° C. to give purified 17α-ethynyl-17β-hydroxyandrost-4-en-3-one melting at about 272.5°–275° C.

EXAMPLE 3

A slurry is prepared from 81 parts of 17α-ethynyl-17β-hydroxyandrost-4-en-3-one, 0.016 part of bromophenol blue, 175 parts of ethyl acetate, 95 parts of ethylene glycol, and 114 parts of ethyl orthoformate. The mixture is heated to 60° C. with stirring and there is added a solubion prepared from 0.2 part of concentrated sulfuric acid and 3.14 parts of tetrahydrofuran. The temperature of the resulting mixture is then maintained at 60° for about 70 minutes. Then, 2.2 parts of tetramethylguanidine is added and the mixture is cooled at 25° C. The solid which is present is then separated by filtration and washed with ethyl acetate that has been saturated with water, until the blue color is removed and the washes are colorless. The resulting solid is then dried at 60° C. to give 3,3-ethylenedioxy-17α-ethynylandrost-5-en-17β-ol containing about 25% of the corresponding 4-ene and melting at about 245°–250° C.

EXAMPLE 4

A mixture is prepared from 115 parts of tetrahydrofuran, 32.5 parts of butyl vinyl ether, 0.01 part of bromophenol blue, 80.9 parts of 3,3-ethylenedioxy-17α-ethynylandrost-5-en-17α-ol, (containing about 25% of the 4-ene) and 0.07 part by volume of methanesulfonic acid diluted with 1 part of tetrahydrofuran. The mixture is stirred gently at 25°–27° C. until the solution becomes clear and then stirred 10 minutes longer. The mixture is now a solution of 17β-(1-butoxyethoxy)-3,3-ethylenedioxy-17α-ethynylandrost-5-ene also containing about 25% of the coresponding 4-ene.

To the above solution is added 6.8 parts of sodium methoxide and this is followed by the addition of 1.2 parts by volume of a 1.5 M solution of 1,3-diphenyl-2-azapropene in benzene. The mixture is refluxed with slow stirring and 78.6 parts of 3 M solution of methylmagnesium chloride in tetrahydrofuran is added over a period of 30 minutes. The mixture does not have a permanent red color at this point. Then, additional methylmagnesium chloride solution is added at a rate of 0.7 part per minute until a pink color appears and develops to give a red solution. The resulting solution is refluxed for an additional 30 minutes and then cooled to −15° C. Then, 10 parts of carbon dioxide is introduced over a period of about 70 minutes while the temperature is maintained below 5° C. and the mixture is stirred rapidly. An additional 5.2 parts of carbon dioxide is added while the temperature is allowed to rise to 15° C. The resulting mixture is then stirred for 15 minutes. Then, a solution is prepared from 15 parts of 85% potassium hydroxide and 21.8 parts of citric acid in 90.8 parts of water and this is cooled to 25° C. and then added to the main reaction mixture while the temperature is allowed to rise to 35°–40° C. Then, 90.5 parts by volume of hexane is added and the mixture is stirred at about 40° C. for about 10 minutes. The aqueous layer is then removed and the organic layer is washed twice with a solution of 19 parts of sodium chloride in 52.7 parts of water. Then, 34.2 parts of anhydrous potassium carbonate and 4.3 parts of diatomaceous earth is added to the organic layer and it is stirred and refluxed for 60 minutes. It is then cooled to about 25°–30° and filtered through diatomaceous earth and the filter cake is washed with a mixture of hexane and tetrahydrofuran. The filtrates are combined and 60 parts of anhydrous potassium carbonate is added and the mixture is stirred well.

A mixture is prepared from 35.8 parts of dimethyl sulfate and 0.002 part of thymol blue and this is cooled to 10° C. and tetramethylguanidine is added until the liquid turns yellow. This mixture is then added all at once to the mixture obtained in the preceding paragraph and the resulting mixture is stirred for 30 minutes. The temperature rises to 35°–40° C. during this time and it is further heated to 50°–55° C. and stirred at this temperature for another 30 minutes. Then, a solution of 3.5 parts of concentrated ammonium hydroxide in 86.5 parts of water is added and the mixture is stirred well for 15 minutes. The organic layer is then separated, washed with brine and dried over anhydrous potassium carbonate at diatomaceous earth. Then, 0.11 parts of tributylamine is added and the mixture is filtered through diatomaceous earth and the filter cake is washed with a mixture of tetrahydrofuran and hexane. The mixture is then heated to distill off the solvent and leave a residual oil which is methyl 17β-(1-butoxyethoxy)-3,3-ethylenedioxy-17α-pregn-5-en-20-yne-21-carboxylate which contains about 25% of the corresponding pregn-4-ene.

The resulting oil is mixed with 909 parts of tetrahydrofuran, 8.05 parts by volume of trimethyl orthoformate, 21.5 parts of ethylene glycol and 0.005 part of bromophenol blue. This mixture is stirred gently and cooled to −10° C. and a mixture of 0.58 part of concentrated sulfuric acid in 2.57 parts of tetrahydrofuran is added. The mixture is stirred gently for 3 hours at −10° C. A solid forms during the first hour. Then, 1.65 parts by volume of tetramethylguanidine is added followed by the addition of 0.2 parts by volume of tetramethylguanidine in 77.8 parts of methanol. Then, 340 parts of water is added while the temperature is maintained below 10° C. The solid is separated by filtration and washed well with cold water and then dried at 60° C. to give methyl 3,3-ethylenedioxy-17β-hydroxy-17α-pregn-5-en-20-yne-21-carboxylate containing approximately 25% of the corresponding pregn-4-ene and melting at about 170°–184°.

EXAMPLE 5

A mixture is prepared from 5.93 parts of lithium hydroxide monohydrate, 163 parts of methanol, 0.4 parts by volume of triethylamine and 40 parts of methyl 3,3-ethylenedioxy-17β-hydroxy-17α-pregn-5-en-20-yne-21-carboxylate (containing about 25% of the 4-ene) and this is heated and stirred at 50° C. for 30 minutes.

Nickel boride catalyst is prepared in the following way. A mixture of 2 parts of nickel chloride hexahydrate and 0.056 part of chromium chloride hexahydrate in 11.8 parts of methanol is stirred under nitrogen and cooled to 5°–10° C. Then a solution of 0.7 part of sodium borohydride in 1.4 parts of water and 5.6 parts of methanol is added slowly, keeping the temperature below 15° C. The resulting slurry is stirred for several minutes to ensure complete decomposition of excess borohydride and then a mixture of 0.2 part of nickel chloride hexahydrate in 5.8 parts of methanol is added and the mixture is stirred at 10°–15° C. for 30 minutes. 8.4 Parts of methanol is used to add the resulting catalyst slurry to a catalytic hydrogenator which already contains the steroid solution obtained in the preceding paragraph. The resulting mixture is then hydrogenated at a pressure of 50 psi and a temperature of 50° C. When hydrogen uptake ceases, stirring is continued at 50° C. for an additional 15 minutes. The hydrogenator is then cooled to 40°–42° C. and, after the hydrogen gas is vented and replaced with nitrogen, 17.1 parts of concentrated hydrochloric acid is added to the mixture and the temperature rises to 50° C. The mixture is then stirred at 50°–55° C. for twenty minutes and then a mixture of 2.67 parts of triethylamine, 1.61 parts of glacial acetic acid and 4 parts of methanol is added. The mixture is then cooled to 25°–30° C. and filtered through diatomaceous earth to remove the catalyst. The methanol is then distilled from the solution and the residual material is cooled to about 35° C. with gentle stirring to allow crystallization. After crystallization has occurred, 125 parts of water is added slowly with stirring. The mixture is then distilled under vacuum to remove the remaining methanol before it is cooled to 30° C. The solid is then separated by filtration and dried at 60° C. to give 17β-hydroxy-3-oxo-17α-pregn-4-ene-21-carboxylic acid γ-lactone.

EXAMPLE 6

A mixture of 8 parts of 85% potassium hydroxide pellets and 33.0 parts of methanol is stirred until the potassium hydroxide dissolves and the resultant solution is then cooled to room temperature. To this solution there is added slowly, with stirring, 13.3 parts of tetramethylammonium chloride. The resulting mixture is heated to 45° C. and stirred for 15 minutes. Then it is cooled to room temperature and filtered to remove the potassium chloride. The potassium chloride is washed with 7.9 parts of methanol and the washings are combined with the original filtrate. The filtrate is then mixed with 0.12 part of lithium hydroxide monohydrate and 11.5 parts of water. A further 10.5 parts of methanol is added and the mixture is stirred under a nitrogen atmosphere as 40 parts of methyl 3,3-ethylenedioxy-17β-hydroxy-17α-pregn-5-en-20-yne-21-carboxylate (containing about 25% of the 4-ene) is added. The mixture is heated at 50° C. for 40 minutes to give a slurry of the tetramethylammonium salt of the steroidal acid which is then cooled to room temperature.

A mixture is prepared from two parts of nickel on alumina catalyst and 16.4 parts of methanol and this is stirred and heated to reflux. Then, during a period of about 3 minutes, 2.4 parts by volume of hydrazine hydrate (85%) is added and the mixture is stirred at just below reflux temperature for 35–40 minutes until gas evolution has nearly stopped. The resulting slurry is then cooled to room temperature and is added to the mixture obtained in the preceding paragraph. 16 Parts of methanol is used to aid in the transfer and a final 106 parts of methanol is added to the reaction mixture. The reaction vessel is vented 3 times with nitrogen and then twice with hydrogen before the mixture is hydrogenated at a temperature of 50° C. and a pressure of 50 lbs. per square inch. When hydrogen uptake ceases, the mixture is stirred at 50° C. for an additional 30 minutes. The mixture is then filtered at 45°–50° C. through diatomaceous earth to remove the catalyst and the catalyst is washed with 20 parts of methanol. To the combined filtrates at 40°–42° C. there is added 15.6 parts of concentrated hydrochloric acid. This brings the pH to 1.0–1.5 and the temperature to 50° C. The reaction mixture is stirred at 50°–55° C. for 20 minutes before a mixture of 4 parts of triethylamine, 2.5 parts of glacial acetic acid and 4.4 parts of methanol is added until the mixture reaches a pH of 4.5–5.0. The methanol solvent is then distilled off until a pot temperature of 78° C. is reached. Then the solution is cooled to about 35° C. with gentle stirring. Crystallization occurs during this time and then 125 parts of water is added slowly with stirring. The mixture is heated again to distill off the remainder of the methanol and then cooled to 30° C. The solid product present is separated by filtration and washed well with cold water. The solid is then further dried at 60° C. to give 17β-hydroxy-3-oxo-17α-pregn-4-ene-21-carboxylic acid γ-lactone.

EXAMPLE 7

The procedure described in the first paragraph of Example 6 is repeated to give a slurry of the tetramethylammonium salt of 3,3-ethylenedioxy-17β-hydroxy-17α-pregn-5-en-20-yne-21-carboxylic acid. Then a slurry of 2 parts of nickel on alumina catalyst in 4 parts of methanol is added to the mixture followed by a slurry of 0.52 parts of potassium borohydride in 4 parts of methanol. Next, a mixture of 1.8 parts of concentrated ammonium hydroxide in 8 parts of methanol is added followed by 121 parts of methanol. The resulting mixture is then hydrogenated and the product is isolated as described in Example 6 to give 17β-hydroxy-3-oxo-17α-pregn-4-ene-21-carboxylic acid γ-lactone.

EXAMPLE 8

A mixture of 41.5 parts of methyl 3,3-ethylenedioxy-17β-hydroxy-17α-pregn-5-en-20-yne-21-carboxylate (containing about 25% of the 4-ene), 4.0 parts of nickel on alumina catalyst and 89 parts of tetrahydrofuran is placed in a hydrogenation vessel. 0.54 Parts of potassium borohydride is slurried with 8 parts of methanol, 1.8 parts of concentrated ammonium hydroxide is added, and the resulting slurry is added to the hydrogention vessel which is then purged with nitrogen and filled with hydrogen to a pressure of 50 psi. Hydrogenation is effected at 60° C. and 50 psi until hydrogen uptake ceases. The mixture is then cooled and the catalyst is removed by filtration. The filtrate is made acidic by the addition of 3.0 parts of concentrated hydrochloric acid and the mixture is kept at 55° C. for 20 minutes. Then, 50 parts of water is added and the pH is adjusted to 4.0 by the addition of 14 parts by volume of a solution obtained by mixing 12.6 parts of triethylamine, 50 parts of water and 7.1 parts of glacial acetic acid. The resulting mixture is distilled to a pot temperature of 77.5° C. to remove most of the organic solvents. It is then cooled to 64° C. to start crystallization and then cooled further to 32° C. to complete the solidification. 300 parts of water is added to the mixture and it is heated to 82° C. under vacuum to remove the remaining organic solvent. The mixture is then cooled to 25° C. and the resulting solid product is separated by filtration, washed thoroughly with water, and dried at about 70° C. to give 17$\beta$-hydroxy-3-oxo-17$\alpha$-pregn-4-ene-21-carboxylic acid $\gamma$-lactone.

EXAMPLE 9

17$\beta$-(1-Butoxyethoxy)-3,3-ethylenedioxy-17$\beta$-ethynylandrost-5-ene is prepared from 137 parts of 3,3ethylenedioxy-17$\alpha$-ethynylandrost-5-ene-17$\beta$-ol according to the procedure described in Example 4. The resulting solution is cooled to −20° to −15° C. under nitrogen and 0.1 part of 1.5 M solution of 1,3-diphenyl-2-azapropene in benzene is added. Then, with stirring, a 2 M solution of butyllithium in hexane is added while keeping the temperature below −15° C. until the mixture takes on a grape-like color. Approximately 150 parts by volume of the butyllithium solution are required. The resulting solution is then saturated with carbon dioxide while the temperature is kept below 0° C. When the exothermic reaction is completed, the mixture is warmed to 20°–25° C. and passage of carbon dioxide into the solution is continued for an additional 30 minutes to give a solution of lithium 17$\alpha$-(1-butoxyethoxy)-3,3-ethylenedioxy-17$\alpha$-pregn-5-en-20yne-21-carboxylate.

A solution of 83 parts of potassium carbonate in 75 parts of water is added to the solution obtained in the preceding paragraph and the resulting mixture is stirred at reflux for 30 minutes. The mixture is then cooled to 30° C. and filtered through diatomaceous earth to remove precipitated lithium carbonate. The precipitate is rinsed with 180 parts by volume of a 1:1 mixture of tetrahydrofuran and hexane. The lower aqueous layer is removed from the combined filtrates and the organic layer is mixed with 80 parts of solid potassium carbonate. Then 35.6 parts by volume of dimethyl sulfate, neutralized with tetramethylguanidine according to the procedure described in Example 4, is added to the stirred mixture. Stirring is continued for 40 minutes, during which time the temperature rises from 31° to 40° C. The mixture is then warmed to 50° C. for an additional 45 minutes before a mixture of 114 parts of water and 4.6 parts of concentrated ammonium hydroxide is added and the mixture is further stirred at 45° C. for 20–25 minutes. This gives a solution of methyl 17$\beta$-(1-butoxyethoxy)-3,3-ethylenedioxy-17$\alpha$-pregn-5-ene-20-yne-21-carboxylate which is isolated accoring to the procedure described in the penultimate paragraph of Example 4 and is then further hydrolyzed according to the procedure described in the final paragraph of Example 4 to give methyl 3,3-ethylenedioxy-17$\beta$-hydroxy-17$\alpha$-pregn-5-en-20-yne-21-carboxylate.

EXAMPLE 10

A mixture is prepared from 62.5 parts of 17$\alpha$-ethynyl-17$\beta$-hydroxyandrost-4-en-3-one, 132 parts of benzene and 88.2 parts by volume of 1,2-propanediol and a little bromophenol blue indicator is added. The solution becomes blue and the blue color is discharged by the addition of several drops of a solution prepared from 1.8 parts of concentrated sulfuric acid and 8 parts of tetrahydrofuran. Then an additional 3 parts by volume of the sulfuric acid solution is added and the mixture is stirred. To this mixture is further added 96.2 parts by volume of ethyl orthoformate and the mixture is warmed from 22 to 64° C. during 25 minutes during which time the steroid starting material dissolves. About 1.5 parts of triethylamine is then added and the indicator then turns the solution deep blue. The solution is then washed with 3 portions of brine, dried over potassium carbonate and filtered through diatomaceous earth. The solvent is then distilled from the filtrate with the final traces being removed under reduced pressure. This leaves a residual oil which is 3,3-propylenedioxy-17$\alpha$-ethynylandrost-5-en-17$\beta$-ol containing approximately 25% of the corresponding $\Delta$-4 isomer.

The crude product obtained in the preceding paragraphis mixed with 75 parts of tetrahydrofuran and 31 parts by volume of butyl vinyl ether and the mixture is warmed to dissolve the steroid starting material. The mixture is then cooled to 20° C. and a small amount of bromophenol blue indicator is added whereupon the solution turns bluish. A catalyst solution is made up from 0.1 part by volume of methanesulfonic acid and 0.8 part of tetrahydrofuran. This solution is added dropwise to the reaction mixture until the blue color is discharged and then 0.46 parts by volume of the solution is added. The mixture is then kept at 20° C. for 70 minutes before 0.4 parts of treithylamine is added. This gives a solution of 17$\beta$-(1-butoxyethoxy)-3,3-propylenedioxy-17$\alpha$-ethynylandrost-5-ene containing about 25% of the corresponding 4-ene. This mixture is reacted successively with methylmagnesium chloride in tetrahydrofuran, carbon dioxide and dimethyl sulfate, all according to the procedure of Example 4, to give methyl 17$\beta$-(1-butoxyethoxy)-3,3-propylenedioxy-17$\alpha$-pregn-5-en-20-yne-21-carboxylate which contains about 25% of the corresponding pregn-4-ene. The 17-butoxyethoxy group is then removed according to the procedure described in the final paragraph of Example 4, except that the ethylene glycol used in that example is replaced by propylene glycol and the final product is isolated by extraction and then removed of the solvent by distillation to give an oil which is methyl 3,3-propylenedioxy-17$\beta$-hydroxy-17$\alpha$-pregn-5-en-20-yne-21-carboxylate containing approximately 25% of the corresponding pregn-4-ene. Hydrogenation of this material and removal of the 3,3-propylenedioxy group according to the procedure described in Example 5 gives 17$\beta$-hydroxy-3-oxo-17$\alpha$-pregn-4-ene-21-carboxylic acid $\gamma$-lactone.

EXAMPLE 11

If the procedure of the first paragraph of Example 4 is repeated using 30.5 parts by volume of ethyl vinyl ether in place of the butyl vinyl ether, the product obtained is 17$\beta$-(1-ethoxyethoxy)-3,3-ethylenedioxy-17$\alpha$-ethynylandrost-5-ene containing about 25% of the corresponding 4-ene. 17α-(1-Methoxyethoxy)-3,3-ethylenedioxy-17α-ethynylandrost-5-ene is prepared in a similar manner except that, in this instance, 115 parts of tetrahydrofuran is cooled to 20° C. and 18.7 parts of methyl vinyl ether gas are dissolved in it and the reaction with 80.9 parts of 3,3-ethylenedioxy-17α-ethynylandrost-5-en-17β-ol is then carried out as before.

17β-(1-Ethoxyethoxy)-3,3-ethylenedioxy-17α-ethynylandrost-5-ene and 17β-(1-methoxyethoxy)-3,3-ethylenedioxy-17α-ethynylandrost-5-ene are each reacted successively with methylmagnesium chloride, carbon dioxide and dimethyl sulfate accoring to the procedure described in Example 4 to give, respectively, methyl 17β-(1-ethoxyethoxy)-3,3-ethylenedioxy-17α-pregn-5-en20-yne-21-carboxylate and 17β-(1-methoxyethoxy)-3,3-ethylenedioxy-17α-pregn-5-en-20-yne-21-carboxylate, both containing about 25% of the corresponding pregn-4-ene. Removal of the 17-protecting group from both of the compounds according to the procedure described in the final paragraph of Example 4 gives methyl 3,3-ethylenedioxy-17β-hydroxy-17α-pregn-5-en-20-yne-21-carboxylate containing approximately 25% of the corresponding pregn-4-ene.

What is claimed is:

1. A process for the preparation of 17β-hydroxy-3-oxo-17α-pregn-4-ene-21-carboxylic acid γ-lactone which comprises:
   a. Reacting 17α-ethynyl-17β-hydroxyandrost-4-en-3-one with an appropriate vic-glycol containing up to 6 carbon atoms to give the corresponding 3,3-[vic-(lower alkylene)dioxy] 5- or 4-unsaturated compound;
   b. Reacting the ketal with a (lower alkyl) vinyl ether in the presence of an acid catalyst to give the corresponding 17β-[1-(lower alkoxy)ethoxy]-3,3-[vic-(lower alkylene)dioxy]-17α-ethynylandrost-(5- or 4-) ene;
   c. Reaction of the ketal-acetal with an alkyl lithium or a Grignard reagent followed by treatment with carbon dioxide to give the corresponding salt of 17β-[1-(lower alkoxy)ethoxy]-3,3-[vic-(lower alkylene)dioxy]-17α-pregn-(5- or 4-)en-20-yne-21-carboxylic acid;
   d. Conversion of the acid salt to the corresponding methyl ester followed by removal of the (lower alkoxy)-ethoxy group to give methyl 3,3-[vic-(lower alkylen)dioxy]-17β-hydroxy-17α-pregn-(5- or 4-)en-20-yne-21-carboxylate;
   e. Catalytic hydrogenation of the ester followed by acidification to give the desired final product.

2. A process according to claim 1 wherein the starting material is obtained by the reaction of androst-4-ene-3,17-dione with pyrrolidine to give 3-(1-pyrrolidinyl)androsta-3,5-dien-17-one followed by ethynylation using potassium hydroxide and acetylene to give 3-(1-pyrrolidinyl)-17α-ethynylandrosta-3,5-dien-17β-ol, followed by removal of the pyrrolidinyl group to give the desired 17α-ethynyl-17β-hydroxyandrost-4-ene-3-one.

3. A process according to claim 1 for the preparation of 17β-hydroxy-3-oxo-17α-pregn-4-ene-21-carboxylic acid γ-lactone which comprises:
   a. Reacting 17α-ethynyl-17β-hydroxy-androst-4-en-3-one with ethylene glycol to give 3,3-ethylenedioxy-17α-ethynylandrost-5-en-17β-ol;
   b. Reacting the ketal with butyl vinyl ether in the presence of an acid catalyst to give 17β-(1-butoxyethoxy)-3,3-ethylenedioxy-17α-ethynylandrost-5-ene;
   c. Reaction of the ketal-acetal with methylmagnesium chloride to give the corresponding ethynylmagnesium chloride derivative, followed by treatment with carbon dioxide to give the magnesium chloride salt of the corresponding 21-carboxylic acid;
   d. Conversion of the magnesium chloride salt to the corresponding potassium salt by means of potassium hydroxide and citric acid followed by potassium carbonate and reaction with dimethyl sulfate to give methyl 17β-(1-butoxyethoxy)-3,3-ethylenedioxy-17α-pregn-5-en-20-yne-21-carboxylate;
   e. Reaction of the methyl ester with acid in the presence of ethylene glycol to give methyl 3,3-ethylenedioxy-17β-hydroxy-17α-pregn-5-ene-20-yne-21-carboxylate;
   f. Catalytic hydrogenation of the 17-hydroxy ester using nickel boride catalyst and a solution strongly alkaline with lithium hydroxide followed by treatment with a strong acid to give the desired 17β-hydroxy-3-oxo-17α-pregn-4-ene-21-carbocylic acid γ-lactone.

4. A process for the preparation of 17β-hydroxy-3-oxo-17α-pregn-4-ene-21-carboxylic acid γ-lactone according to claim 3 wherein the starting material is obtained according to the procedure of claim 2.

5. A compound of the formula

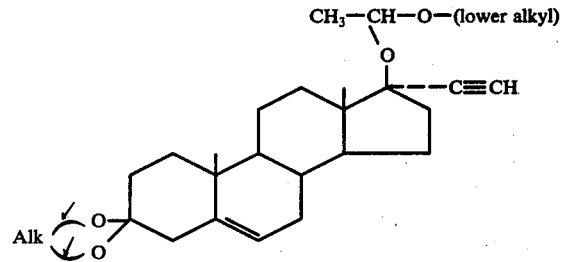

wherein Alk is vic-(lower alkylene).

6. A compound according to claim 5 which is 17β-(1-butoxyethoxy)-3,3-ethylenedioxy-17α-ethynyl-androst-5-ene.

7. A compound according to claim 5 which is 17β-(1-butoxyethoxy)-3,3-propylenedioxy-17α-ethynyl-androst-5-ene.

8. A compound of the formula

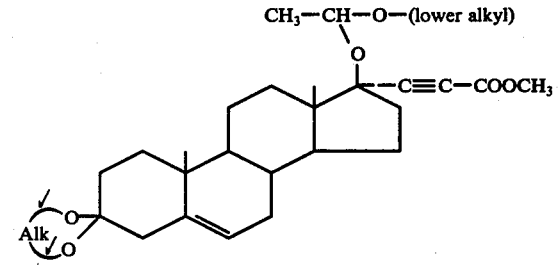

wherein Alk is vic-(lower alkylene).

9. A compound according to claim 8 which is methyl 17β-(1-butoxyethoxy)-3,3-ethylenedioxy-17α-pregn-5-en-20-yne-21-carboxylate.

10. A compound according to claim 8 which is methyl 17β-(1-butoxyethoxy)-3,3-propylenedioxy-17α-pregn-5-en-20-yne-21-carboxylate.

11. Methyl 3,3-ethylenedioxy-17β-hydroxy-17α-pregn-5-en-20-yne-21-carboxylate.

* * * * *